United States Patent [19]

Sharifian et al.

[11] Patent Number: 4,917,781
[45] Date of Patent: Apr. 17, 1990

[54] PROCESS FOR PREPARING QUATERNARY AMMONIUM HYDROXIDES

[75] Inventors: Hossein Sharifian; Alan R. Tanner, both of Austin, Tex.

[73] Assignee: Southwestern Analytical Chemicals, Inc., Austin, Tex.

[21] Appl. No.: 221,720

[22] Filed: Jul. 20, 1988

[51] Int. Cl.$^4$ ............................................. C25B 3/00
[52] U.S. Cl. .................................. 204/72; 204/59 R; 204/102; 204/130; 204/250; 204/251; 204/292; 204/293
[58] Field of Search ........ 204/59 R, 72, 102, 250–251, 204/292–293, 130

[56] References Cited

U.S. PATENT DOCUMENTS

| | | | |
|---|---|---|---|
| 3,523,068 | 8/1970 | Eisenhauer et al. | 204/72 |
| 4,394,226 | 7/1983 | Wade et al. | 204/72 |
| 4,425,202 | 1/1984 | Sullivan | 204/72 |
| 4,521,285 | 6/1985 | De Witt et al. | 204/72 |
| 4,572,769 | 2/1986 | Shimizu | 204/59 R |
| 4,578,161 | 3/1986 | Buonomo et al. | 204/102 |
| 4,714,530 | 12/1987 | Hale et al. | 204/131 |

FOREIGN PATENT DOCUMENTS 57-155390 of 1982 Japan.
60-100690 of 1985 Japan.
60-131985 of 1985 Japan.
60-131986 of 1985 Japan.

OTHER PUBLICATIONS

Morrison & Boyd, *Organic Chemistry*, 3rd Edition, 1974, pp. 752–753.

Primary Examiner—John F. Niebling
Assistant Examiner—David G. Ryser
Attorney, Agent, or Firm—Renner, Otto, Boisselle & Sklar

[57] ABSTRACT

A process is described for preparing quaternary ammonium hydroxides of improved purity. In one embodiment, the present invention relates to a process of preparing quaternary ammonium hydroxides from the corresponding quaternary ammonium salts in an electrolytic cell which comprises an anolyte compartment containing an anode and a catholyte compartment containing a cathode and water, said anolyte and catholyte compartments being separated from each other by a cation-exchange membrane, said process comprising the steps of (a) providing the catholyte compartment with a cathode of zinc, cadmium, tin, lead, or alloys thereof, mercury, or mercury amalgam,
(b) charging an aqueous solution containing a quaternary ammonium salt to the anolyte compartment,
(c) passing a current through the electrolytic cell to produce quaternary ammonium hydroxide in the catholyte compartment, and
(d) recovering the quaternary ammonium hydroxide from the catholyte compartment.

26 Claims, 1 Drawing Sheet

PROCESS FOR PREPARING QUATERNARY AMMONIUM HYDROXIDES

TECHNICAL FIELD

This invention relates to a method of preparing high purity quaternary ammonium hydroxides. The invention also relates to the improved high purity quaternary ammonium hydroxides obtained by the above method.

BACKGROUND OF THE INVENTION

Quaternary ammonium hydroxides such as tetramethylammonium hydroxide (TMAH) and tetraethylammonium hydroxide (TEAH) are strong organic bases that have been known for many years. Such quaternary ammonium hydroxides have found a variety of uses including use as a titrant for acids in organic solvents and as a supporting electrolyte in polarography. Aqueous solutions of quaternary ammonium hydroxides, particularly TMAH solutions, have been used extensively as a developer for photoresists in printed circuit board and microelectronic chip fabrication. Use of quaternary ammonium hydroxides in the electronics area requires that there be no residue following the normal post-bake period. In electronic applications, it is desirable that the aqueous solutions of quaternary ammonium hydroxides should be essentially free from metal ions such as sodium and potassium, and halides such as chlorine, bromine, iodine, etc. Particularly in recent years, there has been an increasing demand for quaternary ammonium hydroxides having a high purity.

Quaternary ammonium hydroxides such as TMAH and TEAH have been produced by various techniques. Generally, the quaternary ammonium hydroxides are manufactured by electrolyzing a salt of a quaternary ammonium compound in an electrolysis cell containing a diaphragm formed of a cation-exchange membrane. The quaternary ammonium salts used in such preparations include halogenated salts, carboxylate salts, carbonate salts and sulfate salts. When halide salts are used in the manufacture of quaternary ammonium hydroxide, it has been discovered that the quaternary ammonium hydroxide solutions formed by this method generally contain significant amounts of halogen (ionic and latent), generally in concentrations above 50 ppm and more generally above 100 ppm. The term "latent halide" is used throughout this specification and claims to refer to non-ionic halide which is present in the aqueous quaternary ammonium hydroxide solutions, and which is capable of forming halide ions under certain conditions such as, e.g., heating.

Among the prior art patents which describe the preparation of quaternary ammonium hydroxides by electrolyzing a salt of a quaternary ammonium compound are U.S. Pat. Nos. 4,572,769, 4,521,285, 4,425,202 and 4,394,226. U.S. Pat. No. 4,572,769 describes the use of formate salts to form the quaternary ammonium hydroxides, and this patent suggests that some of the problems of using quaternary ammonium halides are minimized by use of the formate salt. U.S. Pat. No. 4,521,285 describes an electrolyte process for removing the anion from quaternary organic salts. The process uses a cell comprising four compartments containing two cation exchange membranes and one anion exchange membrane. U.S. Pat. No. ,4,425,202 describes a process for making choline base by electrolysis of choline chloride in an electrolytic cell. Color stabilization of choline base is effected through concentration control and/or the addition of a sulfite prior to electrolytic manufacture of the choline base. U.S. Pat. No. 4,394,226 describes production of quaternary ammonium hydroxides in electrolytic cells using cationic membranes which have been treated with a mineral acid prior to use in the electrolysis.

U.S. Pat. No. 4,714,530 describes an electrolytic process for preparing high purity quaternary ammonium hydroxides which utilizes a cell containing a catholyte compartment and an anolyte compartment separated by a cation-exchange membrane. The process comprises charging an aqueous solution of a quaternary ammonium hydroxide to the anolyte compartment, adding water to the catholyte compartment, and passing a direct current through the electrolysis cell to produce a higher purity quaternary ammonium hydroxide in the catholyte compartment which is subsequently recovered. The '530 patent also describes an improvement which comprises heating the quaternary ammonium hydroxide at an elevated temperature prior to charging the hydroxide to the anolyte compartment of the electrolytic cell.

SUMMARY OF THE DISCLOSURE

A process is described for preparing quaternary ammonium hydroxides of improved purity. In one embodiment, the present invention relates to a process of preparing quaternary ammonium hydroxides from the corresponding quaternary ammonium salts in an electrolytic cell which comprises an anolyte compartment containing an anode and a catholyte compartment containing a cathode and water, said anolyte and catholyte compartments being separated from each other by a cation-exchange membrane, said process comprising the steps of (a) providing the catholyte compartment with a cathode of zinc, cadmium, tin, lead, or alloys thereof, mercury, or mercury amalgam, (b) charging an aqueous solution containing a quaternary ammonium salt to the anolyte compartment, (c) passing a current through the electrolytic cell to produce quaternary ammonium hydroxide in the catholyte compartment, and (d) recovering the quaternary ammonium hydroxide from the catholyte compartment.

In another embodiment, the aqueous solution containing the quaternary ammonium hydroxide prepared and recovered in the above process is further processed by (b) charging said recovered quaternary ammonium hydroxide solution into the anolyte compartment of a second electrolytic cell comprising an anolyte compartment and a water-containing catholyte compartment separated by a cation-exchange membrane, (c) passing a current through the second electrolytic cell for a period of time sufficient to form quaternary ammonium hydroxide in the catholyte compartment, and (d) recovering the quaternary ammonium hydroxide solution from the catholyte compartment, said solution containing a quaternary ammonium hydroxide of higher purity than the quaternary ammonium hydroxide solution charged to the anolyte compartment of the second electrolytic cell in step (b).

The process of this embodiment using two electrolytic cells results in the formation of quaternary ammonium hydroxide solutions containing significantly reduced amounts of halogen (both ionic and latent), carbonates and/or metals.

BRIEF DESCRIPTION OF THE DRAWING

The sole FIGURE is a schematic cross-sectional drawing of a typical electrolytic cell useful in performing the process of the invention.

DESCRIPTION OF THE PREFERRED EMBODIMENTS

Figure 1:
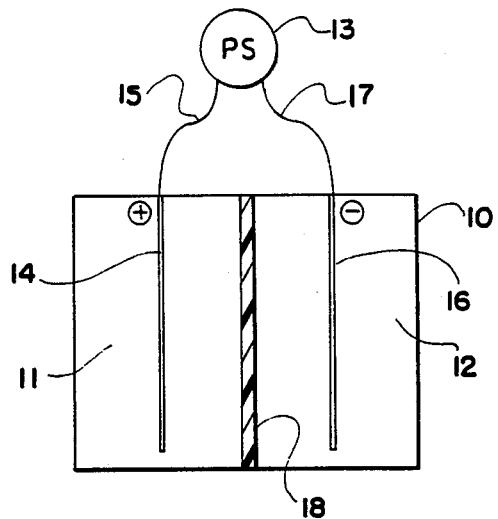

As noted, the quaternary ammonium hydroxides which are prepared in accordance with the process of the present invention are derived from the corresponding quaternary ammonium salts. The quaternary ammonium salts may generally be characterized by the formula $A^+X^-$ wherein $A^+$ is a quaternary ammonium cation and $X^-$ is an anion such as a halide ion, alkyl sulfate anion, a carboxylic acid anion, etc. The halide ions include chlorine, fluorine, bromine and iodine. An example of an alkyl sulfate anion is methyl sulfate ($CH_3SO_4^-$), and examples of carboxylic acid ions include the formate and acetate anions.

In one embodiment of the present invention, the quaternary ammonium salt is characterized by the formula

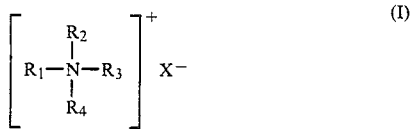

wherein $R_1$, $R_2$, $R_3$ and $R_4$ are each independently alkyl groups containing from one to about 10 carbon atoms, hydroxyalkyl groups containing from 2 to about 10 carbon atoms, alkoxyalkyl groups containing from two to about 10 carbon atoms, aryl groups, or hydroxyaryl groups and X is a halogen or $R_5COO$ wherein $R_5$ is hydrogen or a methyl group.

Specific examples of alkyl groups containing from one to 10 carbon atoms include methyl, ethyl, propyl, butyl, pentyl, hexyl, heptyl, octyl, nonyl, and decyl groups. $R_1$, $R_2$, $R_3$ and $R_4$ also may be hydroxyalkyl groups such as hydroxyethyl and the various isomers of hydroxypropyl, hydroxybutyl, hydroxypentyl, etc. Specific examples of alkoxyalkyl groups include ethoxyethyl, butoxymethyl, butoxybutyl, etc. Examples of various aryl and hydroxyaryl groups include phenyl, benzyl, and equivalent groups wherein benzene rings have been substituted with one or more hydroxy groups.

Specific examples of the anion $X^-$ include the fluoride, chloride, bromide, iodide, formate, acetate, etc. anions. The process of the present invention is particularly useful when the salt is a halide.

Examples of quaternary ammonium salts representative of formula I which can be treated in accordance with the process of the present invention to form quaternary ammonium hydroxides include tetramethylammonium chloride, tetramethylammonium bromide, tetramethylammonium formate, tetramethylammonium acetate, tetraethylammonium chloride, tetraethylammonium bromide, tetraethylammonium formate, tetraethylammonium acetate, tetrapropylammonium chloride, trimethylhydroxyethylammonium chloride, trimethylmethoxyethylammonium chloride, dimethyldihydroxyethylammonium chloride, methyltrihydroxyethylammonium chloride, phenyltrimethylammonium chloride, phenyltriethylammonium chloride, benzyltrimethylammonium chloride, etc.

In one preferred embodiment, the R groups are alkyl groups containing one to three carbon atoms and hydroxyalkyl groups containing from two to three carbon atoms. Most often, the quaternary ammonium salts treated in accordance with the process of the present invention will be tetramethylammonium chloride or tetraethylammonium chloride.

In accordance with the process of the present invention, quaternary ammonium salts such as those described above are converted to quaternary ammonium hydroxides in an electrolytic cell which comprises an anolyte compartment containing an anode and a catholyte compartment containing a cathode of zinc, cadmium, tin, lead, or alloys thereof, mercury, or mercury amalgam, said anolyte and catholyte compartments being separated from each other by a cation-exchange membrane. A schematic cross-sectional representation of such an electrolytic cell suitable for conducting the process of the present invention is shown in FIG. 1. In this FIGURE, the electrolytic cell 10 comprises an anolyte compartment 11 and a catholyte compartment 12 separated from each other by a cation-exchange membrane 18. The anolyte compartment 11 contains anode 14 which is attached to power supply 13 by wire 15. The catholyte compartment 12 contains cathode 16 which is attached to power supply 13 through wire 17. Various materials which have been used as anodes in electrolytic cells can be included in the cells used in the present invention. For example, the anode may be made of metals such as, for example, titanium coated electrodes, tantalum, zirconium, hafnium or alloys of the same. Generally, the anodes will have a non-passivable and catalytic film which may comprise metallic noble metals such as platinum, iridium, rhodium or alloys thereof, or a mixture of electroconductive oxides comprising at least one oxide or mixed oxides of a noble metal such as platinum, iridium, ruthenium, palladium or rhodium.

The cathodes in the electrolytic cells utilized in the process of the present invention comprise zinc, cadmium, tin, lead, mercury, or mercury amalgam. Alloys of zinc, cadmium, tin or lead also can be used as cathode materials. The mercury amalgam cathodes include, for example, mercury on nickel, mercury on copper, mercury on cadmium, mercury on zinc, etc. The use of such cathodes is particularly desirable when the quaternary ammonium salt charged to the anolyte compartment is a halide. It has been discovered that the use of these particular cathode materials results in the formation of quaternary ammonium hydroxides in the catholyte compartment which contain significantly reduced amounts of latent halide.

A preferred embodiment of the process of the present invention utilizing an electrolytic cell of the type described above and shown in FIG. 1 is illustrated by the following representative example. An aqueous solution containing a quaternary ammonium salt such as tetramethylammonium chloride is charged to the anolyte compartment 11, and water is charged to the catholyte compartment 12. An electrical potential is established and maintained by a power source 13 between anode 14 and cathode 16 to produce a flow of current across cell 10 to convert chloride ions into chlorine gas at anode 14, and water to dissociate into hydrogen gas and hydroxide ions at cathode 16. Chlorine gas and hydrogen gas are collected and removed by gas collecting means (not shown). In addition, as a result of the current flow, quaternary ammonium ions migrate from the anode compartment 11 to the cathode compartment 12 through the cation-exchange membrane 18 where the quaternary ammonium ions and the hydroxide ions combine to form a solution of quaternary ammonium hydroxide. The quaternary ammonium hydroxide solution may be removed from the catholyte compartment as desired. The quaternary ammonium salt and water may be periodically or continuously added to the anolyte and catholyte compartments, respectively, to maintain an appropriate concentration of salt in the anolyte and hydroxide in the catholyte compartments.

The concentration of quaternary ammonium salt in the aqueous solution contained in the anolyte compartment may vary over a wide range such as from about 3% to about 55% by weight. Typically, the concentration of the quaternary ammonium salt in the aqueous solution will be from about 5 to about 40% by weight and more generally from about 8 to about 20% by weight.

During the electrolysis, it is generally desirable that the temperature of the liquid within the cell be maintained within a range of from about 10° to about 70° C., and more generally, the temperature is maintained at about 50° C. during the electrolysis.

As noted, the electrolysis cell utilized in the process of the present invention contains a cation-exchange membrane. The cation-exchange membrane may be any of those which have been used in the electrolysis of quaternary ammonium salts to quaternary ammonium hydroxides. Preferably, the cation-exchange membranes should comprise a highly durable material such as the membranes based on the fluorocarbon series, or from less expensive materials of the polystyrene or polypropylene series. Preferably, however, the cationic membranes useful in the present invention include fluorinated membranes containing cation exchange groups such as perfluorosulfonic acid and perfluorosulfonic acid/perfluorocarboxylic acid perfluorocarbon polymer membranes such as sold by the E. I. duPont de Nemours & Company under the trade designation "NAFION". Other suitable cation-exchange membranes include styrene-divinylbenzene copolymer membranes containing cation-exchange groups such as sulfonate groups, carboxylate groups, etc.

The preparation and structure of cationic membranes are described in the Encyclopedia of Polymer Science and Technology, Volume 8, pages 620–638, H. Wiley & Sons, N.Y., 1968. The disclosure of these pages is hereby incorporated by reference.

The electrolysis cell used in the process of the present invention may be any of the known electrolysis cells and is not limited to the type shown in FIG. 1. The cells may be composed of conventional cell materials which are compatible with the materials being charged into the cells.

The water is charged into the catholyte compartment either before or after the aqueous quaternary ammonium salt solution is charged to the anolyte compartment, but the water is charged before electrolysis is initiated. The water is preferably deionized water and more preferably, very pure deionized water. Demineralized water has low electric conductivity. When therefore, the demineralized water is supplied to the cathode chamber, difficulties arise in commencing electrolysis at the start of manufacturing the subject quaternary ammonium hydroxide. It is therefore preferred to apply a demineralized water to which about 0.01 to 1.0% by weight of quaternary ammonium hydroxide is added.

The electrolysis of the aqueous solution containing the quaternary ammonium salt is effected by impressing a current voltage (generally direct current voltage) between the anode and cathode with a current density of from about 5 to about 250 A/ft$^2$, and more preferably at a current density of from about 25 to about 150 A/ft$^2$. Alternatively the current density may be about 1–100 A/dm$^2$ or 10–50 A/dm$^2$. The current is applied to the cell for a period which is sufficient to result in the formation of the desired concentration of quaternary ammonium hydroxide in the catholyte compartment. Circulation is effected by pumping and/or by gas evolution. In practice, the electrolytic cell can be operated batchwise or in a continuous operation.

The concentration of the quaternary ammonium hydroxide in the aqueous solution formed in the catholyte compartment will range from about 5 to about 40% by weight. In accordance with this invention, when formed from quaternary ammonium halides, the quaternary ammonium hydroxides are characterized as containing much less latent halide and more ionic halide than the corresponding hydroxides prepared using electrolytic cells not containing the cathode material specified in this invention. The quaternary ammonium hydroxide formed in the catholyte compartment also is found to contain lesser amounts of other impurities such as alkaline earth metals, heavy metals, carbonates, etc. A typical product of this embodiment at 25% w of the quaternary ammonium hydroxide contains about 35 ppm of ionic chloride and little or no detectable latent chloride.

In one preferred embodiment, the aqueous solution containing the quaternary ammonium hydroxide which is formed and recovered from the electrolytic cell containing the above specified cathodes is electrolyzed in a second electrolytic cell to improve on the purity of the quaternary ammonium hydroxide in the general manner described in U.S. Pat. No. 4,714,530. In this embodiment, the quaternary ammonium hydroxide which has been prepared from a salt as described above utilizing an electrolytic cell containing one of the above-specified cathode materials is subjected to a second electrolysis by (b) charging said recovered quaternary ammonium hydroxide solution into the anolyte compartment of a second electrolytic cell comprising an anolyte compartment and a water-containing catholyte compartment separated by a cation-exchange membrane, (c) passing a current through the electrolytic cell for a period of time sufficient to form quaternary ammonium hydroxide in the catholyte compartment, and (d) recovering the quaternary ammonium hydroxide solution from the catholyte compartment, said solution containing a quaternary ammonium hydroxide of higher purity than the quaternary ammonium hydroxide solution charged to the anolyte compartment of the second electrolytic cell in step (b).

The second electrolytic cell utilized in the above process may be identical to the first electrolytic cell in which the quaternary ammonium salt is converted to a quaternary ammonium hydroxide although it is not necessary to use a zinc, cadmium, lead, mercury or mercury amalgam cathode in the second electrolytic cell. The cathode of the second electrolytic cell may comprise any material normally used in electrolytic processes such as solid nickel, nickel alloys, iron and stainless steel.

The process for purifying the quaternary ammonium hydroxide solution in the second electrolytic cell is conducted under the same conditions of temperature and time as described above for the first electrolytic process for converting the salts to hydroxides. The concentration of the quaternary ammonium hydroxide solution charged into the anolyte compartment of the second electrolytic cell generally will be from about 3 to about 55%, more often, from about 5 to about 40% by weight. Concentrations of the quaternary ammonium hydroxide in water of from about 8 to about 15% by weight are particularly useful. As noted above, the quaternary ammonium hydroxides prepared from the salts in accordance with the procedure of the present invention as described above contain little or no latent halide, and the concentration of ionic halide may range from about 15 to about 200 ppm. More often, the concentration of ionic halide in quaternary ammonium hydroxides prepared from quaternary ammonium halides in accordance with the process of the present invention will contain from about 15 to about 50 or 75 ppm of ionic halide. When such ionic halide containing quaternary ammonium hydroxides are treated in a second electrolytic cell in accordance with the present invention, the amount of ionic halide contained in the quaternary ammonium hydroxide produced and recovered from the second electrolytic cell is significantly reduced. The typical properties of a 25% by weight aqueous solution of quaternary ammonium hydroxide purified and recovered from the second electrolytic cell are: zero to 5 or 10 ppm of ionic halide; zero ppm of latent halide; and no detectable heavy metals.

The following examples illustrate the processes of the present invention. Unless otherwise indicated in the following examples, and elsewhere in the specification and claims, all parts and percentages are by weight, all temperatures are in degrees centigrade, and pressure is at or near atmospheric pressure.

EXAMPLE 1

A 1.0M aqueous tetramethylammonium chloride solution is used as the anolyte in a cell equipped with a titanium anode coated with ruthenium oxide, a zinc cathode and a NAFION 901 membrane (duPont). Deionized water containing 1.0% by weight of pure tetramethylammonium hydroxide is added to the catholyte compartment. Electrolysis is carried out at a current density of about 83 A/ft$^2$ and at a temperature of about 50° C. until a 1.45M solution of tetramethylammonium hydroxide is obtained in the catholyte. The tetramethylammonium hydroxide is recovered from the catholyte compartment, and analysis of the recovered tetramethylammonium hydroxide solution at 25% TMAH indicates an ionic chloride concentration of about 35 ppm and no detectable latent chloride.

CONTROL EXAMPLE 1

The general procedure of Example 1 is repeated except that the zinc cathode is replaced by a stainless steel cathode. Electrolysis is conducted at about 83 A/ft$^2$ until a 1.2M tetramethylammonium hydroxide solution is obtained in the catholyte. Recovery and analysis of the tetramethylammonium hydroxide solution obtained in this manner indicates an ionic chloride concentration of 51 ppm and a latent chloride concentration of 32 ppm at 25% TMAH.

EXAMPLE 2

The general procedure of Example 1 is repeated except that the zinc cathode is replaced by a mercury pool cathode.

EXAMPLE 3

The procedure of Example 1 is repeated except that the zinc cathode is replaced by a cadmium cathode.

EXAMPLE 4

The procedure of Example 1 is repeated except that the zinc cathode is replaced by a lead cathode.

EXAMPLE 5

The procedure of Example 1 is repeated except that the zinc cathode is replaced with a mercury amalgamated copper cathode.

EXAMPLE 6

The procedure of Example 1 is repeated except that the zinc cathode is replaced by a mercury amalgamated nickel cathode.

EXAMPLE 7

An aqueous tetramethylammonium hydroxide solution prepared as in Example 1 and containing about 12% by weight of the hydroxide is used as the anolyte in a cell equipped with an iron cathode, ruthenium oxide anode and a NAFION 901 membrane (DuPont). Deionized water containing a small amount (about 0.1%) of a purified form of the quaternary ammonium hydroxide is used as the catholyte. Electrolysis is conducted at about 50° C. and at a current density of about 83 A/ft$^2$. The ionic chloride content of the tetramethylammonium hydroxide solution formed in the catholyte is less than the ionic chloride content of the tetramethylammonium hydroxide charged to the anolyte compartment.

While the invention has been explained in relation to its preferred embodiments, it is to be understood that various modifications thereof will become apparent to those skilled in the art upon reading this specification. Therefore, it is to be understood that the invention disclosed herein is intended to cover such modifications as fall within the scope of the appended claims.

We claim:

1. A process of preparing quaternary ammonium hydroxides from quaternary ammonium salts in an electrolytic cell which comprises an anolyte compartment containing an anode and a catholyte compartment containing a cathode and water, said anolyte and catholyte compartments being separated from each other by a cation-exchange membrane, said process comprising the steps of
   (a) providing the catholyte compartment with a cathode of zinc, cadmium, tin, lead, or alloys thereof, mercury, or mercury amalgam,
   (b) charging an aqueous solution containing a quaternary ammonium salt to the anolyte compartment,
   (c) passing a current through the electrolytic cell to produce quaternary ammonium hydroxide in the catholyte compartment, and
   (d) recovering the quaternary ammonium hydroxide from the catholyte compartment.

2. The process of claim 1 wherein the cathode is a zinc cathode.

3. The process of claim 1 wherein the quaternary ammonium salt is characterized by the formula

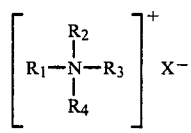

(I)

wherein $R_1$, $R_2$, $R_3$ and $R_4$ are each independently alkyl groups containing from one to about ten carbon atoms, hydroxyalkyl or alkoxyalkyl groups containing from two to about ten carbon atoms, aryl groups, or hydroxyaryl groups, and X is a halide or $R_5COO$ wherein $R_5$ is hydrogen or a methyl group.

4. The process of claim 3 wherein X is a halide.

5. The process of claim 3 wherein $R_1$, $R_2$, $R_3$ and $R_4$ are each independently alkyl groups containing one to three carbon atoms or hydroxyalkyl groups containing two to three carbon atoms.

6. The process of claim 3 wherein $R_1$, $R_2$, $R_3$ and $R_4$ are methyl or ethyl groups.

7. The process of claim 1 wherein the quaternary ammonium salt is a halide.

8. The process of claim 1 wherein the quaternary ammonium salt is a quaternary ammonium chloride.

9. The process of claim 1 wherein the cation-exchange membrane comprises a perfluorosulfonic acid or a perfluorosulfonic acid/perfluorocarboxylic acid perfluorohydrocarbon polymer membrane.

10. The process of claim 1 wherein the concentration of the quaternary ammonium salt in the aqueous solution charged in step (b) is from about 3 to about 55% by weight.

11. The process of claim 1 wherein from about 0.01 to about 1% by weight of a purified quaternary ammonium hydroxide is charged to the catholyte compartment prior to step (c), said hydroxide corresponding to the quaternary ammonium hydroxide prepared in the process.

12. A process of preparing quaternary ammonium hydroxides from quaternary ammonium halides in an electrolytic cell which comprises an anolyte compartment containing an anode, and a catholyte compartment containing a cathode and water, said anolyte and catholyte compartments being separated from each other by a cation-exchange membrane, said process comprising the steps of
(a) providing the catholyte compartment with a cathode of zinc, cadmium, tin, lead, or alloys thereof, mercury, or mercury amalgam,
(b) charging an aqueous solution containing a quaternary ammonium halide to the anolyte compartment wherein said quaternary ammonium halide is characterized by the formula

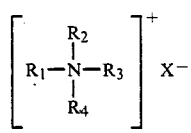

(I)

wherein $R_1$, $R_2$, $R_3$ and $R_4$ are each independently alkyl or hydroxyalkyl groups containing from one to about ten carbon atoms, and X is a halide,
(c) passing a current through said electrolytic cell to form quaternary ammonium hydroxide in the catholyte compartment that is substantially free of latent halide, and
(d) recovering the quaternary ammonium hydroxide from the catholyte compartment.

13. The process of claim 12 wherein the concentration of quaternary ammonium halide in the aqueous solution in the anolyte is from about 3% to about 55% by weight.

14. The process of claim 12 wherein the concentration of quaternary ammonium hydroxide in the aqueous solution recovered in step (d) is between about 5 to about 40% by weight.

15. The process of claim 12 wherein $R_1$, $R_2$, $R_3$ and $R_4$ each contain one or two carbon atoms.

16. The process of claim 12 wherein $R_1$, $R_2$, $R_3$ and $R_4$ are methyl groups.

17. The process of claim 12 wherein the quaternary ammonium halide is a chloride.

18. The process of claim 12 wherein the quaternary ammonium halide is tetramethylammonium chloride.

19. The process of claim 12 wherein from about 0.01 to about 1% by weight of a purified quaternary ammonium hydroxide is charged to the catholyte compartment prior to step (c), said hydroxide corresponding to the quaternary ammonium hydroxide prepared in the process.

20. The process of claim 12 wherein the cathode is a zinc cathode.

21. A process of preparing high purity quaternary ammonium hydroxides from quaternary ammonium salts in an electrolytic cell which comprises an anolyte compartment containing an anode and a catholyte compartment containing a cathode, said anolyte and catholyte compartments being separated from each other by a cation-exchange membrane, said process comprising the steps of
(a) preparing and recovering a quaternary ammonium hydroxide from the corresponding quaternary ammonium salt in accordance with the process of claim 1,
(b) charging said recovered quaternary ammonium hydroxide solution into the anolyte compartment of a second electrolytic cell comprising an anolyte compartment and a water-containing catholyte compartment separated by a cation-exchange membrane,
(c) passing a current through the second electrolytic cell for a period of time sufficient to form quaternary ammonium hydroxide in the catholyte compartment, and
(d) recovering the quaternary ammonium hydroxide solution from the catholyte compartment, said solution containing a quaternary ammonium hydroxide of higher purity than the quaternary ammonium hydroxide solution charged to the anolyte compartment of the second electrolytic cell in step (b).

22. The process of claim 21 wherein the quaternary ammonium salt is a halide represented by the formula

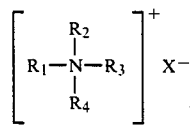

(I)

wherein $R_1$, $R_2$, $R_3$ and $R_4$ are each independently alkyl or hydroxyalkyl groups containing from one to about ten carbon atoms, and X is a halide.

23. The process of claim 22 wherein $R_1$, $R_2$, $R_3$ and $R_4$ are alkyl groups containing from one to three carbon atoms.

24. The process of claim 22 wherein $R_1$, $R_2$, $R_3$ and $R_4$ are methyl groups.

25. The process of claim 22 wherein the halogen is a chloride.

26. The process of claim 21 wherein the concentration of the quaternary ammonium hydroxide in the aqueous solution charged to the anolyte in step (b) is from about 3 to about 55% by weight.

* * * * *